(12) United States Patent
Anderson et al.

(10) Patent No.: US 8,067,432 B2
(45) Date of Patent: Nov. 29, 2011

(54) LIPOSOMAL, RING-OPENED CAMPTOTHECINS WITH PROLONGED, SITE-SPECIFIC DELIVERY OF ACTIVE DRUG TO SOLID TUMORS

(75) Inventors: Bradley D. Anderson, Lexington, KY (US); Vijay Joguparthi, Danbury, CT (US); Tian-Xiang Xiang, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 884 days.

(21) Appl. No.: 12/058,794

(22) Filed: Mar. 31, 2008

(65) Prior Publication Data

US 2009/0246268 A1 Oct. 1, 2009

(51) Int. Cl.
*A61K 31/4745* (2006.01)
*C07D 471/14* (2006.01)

(52) U.S. Cl. ............. 514/285; 546/70; 546/48; 514/283
(58) Field of Classification Search .................. 514/285, 514/283; 546/70, 48
See application file for complete search history.

(56) References Cited

U.S. PATENT DOCUMENTS

| | | |
|---|---|---|
| 5,552,156 A | 9/1996 | Burke |
| 5,736,156 A | 4/1998 | Burke |
| 6,352,996 B1 | 3/2002 | Cao et al. |
| 6,653,319 B1 | 11/2003 | Xiang et al. |
| 6,897,200 B1 | 5/2005 | Burke et al. |
| 7,060,828 B2 | 6/2006 | Madden et al. |
| 7,122,553 B2 | 10/2006 | Rahman et al. |
| 2003/0215492 A1 | 11/2003 | Ahmad et al. |
| 2005/0019387 A1 | 1/2005 | Rahman et al. |
| 2005/0100590 A1 | 5/2005 | Duena et al. |
| 2005/0191344 A1 | 9/2005 | Zalipsky et al. |

FOREIGN PATENT DOCUMENTS

| | | | |
|---|---|---|---|
| EP | 1547580 A1 | * | 6/2005 |
| WO | WO 2004/002454 A1 | * | 1/2004 |

OTHER PUBLICATIONS

Vijay Joguparthi et al., "Liposomal Delivery of Hydrophobic Weak Acids: Enhancement of Drug Retention Using a High Intraliposomal pH," Journal of Pharmaceutical Sciences, vol. 97, No. 1, Jan. 2008, pp. 433-454.
J. Allen Zhang et al., "Development and characterization of a novel liposome-based formuation of SN-38," International of Journal Pharmaceutics 270 (2004) 93-107.
Eric H. Kraut et al., "Final Results of a Phase I Study of Liposome Encapsulated SN-38 (LE-SN38): Safety, Pharmacogenomics, Pharmacokinetics, and Tumor Response," ASCO 2005 Abstract 2017 (LE-SN38-101 Study), 4 pages.
Vigay Joguparthi et al., "Lipid Bilayer Permeability of the Lactone Form of a Lipophillic Camptothecin, DB-67," 2006 AAPS Annual Meeting and Exposition, Oct. 31, 2006, 2 pages.
Vigay Joguparthi et al., "Controlled Release of Camptothecins by Intraliposomal pH Alteration: in Vitro Studies with DB-67," 2006 AAPS Annual Meeting and Exposition, Oct. 28-Nov. 2, 2006, 1 pages.

* cited by examiner

*Primary Examiner* — Charanjit Aulakh
(74) *Attorney, Agent, or Firm* — King & Schlickli, PLLC

(57) ABSTRACT

A method for preparing a stable dispersion of a camptothecin, camptothecin prodrug, or analog thereof for administration to a patient in need thereof includes preparing a solution of the camptothecin, wherein the solution has a pH which places substantially an entirety of that camptothecin in a carboxylate form. The camptothecin may be a neutral camptothecin. The solution is next loaded into a liposome including at least one lipid, which may be a phospholipid. An intraliposomal pH is maintained which preserves substantially an entirety of the camptothecin in the carboxylate form. The liposomal dispersion is administered to an individual in need thereof, whereby the liposomes accumulate at and permeate into tumor tissue and an active, lactone form camptothecin is released in situ at the tumor site. Compositions formulated in accordance with the described method for treatment of a cancer in an animal in need thereof are provided also.

24 Claims, 3 Drawing Sheets

LIPOSOMAL, RING-OPENED CAMPTOTHECINS WITH PROLONGED, SITE-SPECIFIC DELIVERY OF ACTIVE DRUG TO SOLID TUMORS

This invention was made with Government support under NIH/NCI Grant R01-CA-87061. The Government may have certain rights in this invention.

TECHNICAL FIELD

The present invention relates to the field of compositions for treatment of a cancer in an animal, and to methods for preparing such compositions. In particular, the present invention relates to a method for formulating a stable liposomal camptothecin or analog thereof, and to compositions formulated thereby.

BACKGROUND OF THE INVENTION

Structure-activity studies show that successful inhibition of DNA topoisomerase I by camptothecin analogues requires an intact lactone ring (E-ring) functionality. Camptothecin analogs having open lactone ring structures (also known as the carboxylate form or as camptothecin carboxylates) are poorly accumulated by cancer cells, exhibit limited activity against the topoisomerase enzyme, and may be more toxic to healthy cells than the lactone form.

Unfortunately, in aqueous solutions, camptothecins undergo a pH dependent hydrolysis to the inactive carboxylate form (FIG. 1). This, coupled with the fact that the inactive carboxylate form is favored in aqueous solution at pH 7.4 may account for the limited clinical success of certain camptothecins. Even more, under physiological conditions such as in blood, this equilibrium may shift further toward the inactive carboxylate form by preferential carboxylate binding to serum albumin, which affects certain congeners more than others.

Camptothecins may be further subclassified into neutral and cationic camptothecins. Camptothecins which exist primarily as neutral species at pH less than 7 are generally classified as neutral, whereas camptothecins having cationic substituent groups in the parent structure and which exist predominantly as positively charged species at pH less than 7 are classified as cationic camptothecins. Both subspecies of camptothecins undergo chemical degradation by lactone ring hydrolysis to the inactive carboxylate form as described above. It is known that neutral camptothecins are significantly less water-soluble at low pH than their cationic counterparts.

This poor water-solubility has severely limited the types of formulations and drug concentrations of highly lipophilic neutral camptothecinsm, prodrugs and analogs [e.g., 10-hydroxy-7-ethyl camptothecin (SN38), silatecan 7-t-butyldimethylsilyl-10-hydroxycamptothecin (DB-67), karenitecan, gimatecan, irinotecan, 9-nitro camptothecin, and the like] that can be employed for clinical treatment of cancer, even though lipophilic camptothecins and analogs provide several important advantages over their water-soluble counterparts. For example, because of its increased lipophilicity and dual 7-alkylsilyl and 10-hydroxy substitution, DB-67 displays superior binding to cellular and liposomal membranes and enhanced drug stability in the presence of human serum albumin when compared with clinically relevant, more hydrophilic camptothecin analogues. Indeed, in vitro cytotoxicity assays indicate that DB-67 has at least comparable potency with other FDA approved camptothecin analogs (e.g., Camptosar and Hycamtin).

It is known to utilize liposomes as delivery vehicles for camptothecins. Liposomal encapsulation can improve solubility of both neutral and cationic camptothecins, overcoming known water insolubility of camptothecins and analogs and also minimizing side effects of camptothecins relating to their cytotoxicity by more closely targeting delivery to tumor tissue. In addition, it has been shown that liposomes may accumulate in tumor tissue after delivery due to an enhanced permeation and retention effect ((Drummond, D. C., Meyer, O., Hong, K., Kirpotin, D. B., Papahadjopoulos, D. 1999, Optimizing liposomes for delivery of chemotherapeutic agents to solid tumors, Pharmacol. Rev. 51(4): 691-743)), providing a more targeted drug delivery and enabling passive tumor targeting. That is, drug encapsulation in liposomes can improve drug distribution (preferentially to tumor tissue rather than normal tissue) by reducing drug access to normal tissue. Specifically, the enhanced permeability of the microvasculature in tumor tissue allows particles having the size range of a liposome to escape from the blood circulature and collect in tumor tissue. Once in the tumor bed, particles such as liposomes are retained in tumor tissue for an increased period of time.

Camptothecins in the active lactone form partition preferentially into liposomal membranes, thus minimizing exposure to the aqueous environment and decreasing unwanted conversion of the active lactone form to the inactive carboxylate form. For this reason, typically a low intraliposomal pH is maintained to stabilize camptothecins held therein in the active lactone form. This formulation strategy typically requires use of an aqueous buffer and, while effective for cationic camptothecins, is unsuitable for neutral camptothecins due to their reduced water-solubility at low pH as noted above. Accordingly, while liposomal delivery technology is an effective method of delivery for camptothecins, presently it is less suited to delivery of neutral camptothecins due to the difficulties in achieving adequate concentrations of liposome-bound drug, and also to inadequate retention of the lactone form of the drug in liposomes after injection. Indeed, inadequate retention of lactone-form neutral camptothecins in liposomes after delivery to patients limits or eliminates any advantage provided by liposomal delivery compared to conventional dosage forms such as injectable solutions.

Especially for the advantages provided by use of neutral camptothecins compared to cationic camptothecins, that is, enhanced membrane-binding and superior drug stability in the presence of blood components such as albumin, there remains a need in the art for pharmaceutical formulations comprising neutral camptothecins for treatment of various cancers. Such formulations should provide a stable camptothecin formulation, and also improve retention of intraliposomal drug, promoting passive targeting of tumor tissue by liposomes and delivery of increased dosages of drug to such tumor tissue while reducing effects on healthy tissue.

SUMMARY OF THE INVENTION

In accordance with the foregoing identified need, a novel method for preparing a liposomal formulation of a camptothecin, prodrug, or analog thereof, and compositions formulated thereby, are provided. In one aspect, a method is provided for preparing a stable dispersion of a camptothecin, prodrug, or analog thereof for delivery to a patient in need thereof. The method includes preparing a solution of a camptothecin, prodrug, or analog thereof, wherein the solution has a pH which places substantially an entirety of that camptothecin, prodrug, or analog thereof in substantially a ring-opened carboxylate form. Next, the solution is loaded into a liposome having an intraliposomal pH which preserves substantially an entirety of the intraliposomal camptothecin, prodrug, or analog thereof in the ring-opened, carboxylate form. Next is the step of delivering the liposome to a patient in need thereof, whereby the liposome accumulates at a tumor site and the camptothecin, prodrug or analog thereof is released as an active, lactone form in situ at the tumor site.

The solution of camptothecin, prodrug, or analog thereof may be formulated to have a pH of from about 9.0 to about 11.0. In one aspect of the invention, a neutral camptothecin, prodrug, or analog thereof is utilized, including without limitation camptothecin, DB-67, SN-38, gimatecan, karenitecin, irinotecan, 9-nitro camptothecin, and mixtures thereof.

The liposome will typically be formulated to include at least one lipid, typically selected from at least one of a phospholipid and/or a sterol, for example cholesterol. The liposome may further include a sphingolipid. That phospholipid may be a synthetic or a natural phospholipid, and may be an egg phospholipid, a soy phospholipid, distearoylphosphatidyl choline, dipalmitoylphosphatidyl choline, diarachidonoyl phosphatidyl choline, hydrogenated soy phosphatidyl choline, dimyristoylphosphatidyl glycerol, dioleylphosphatidylglycerol, dimyristoylphosphatidylcholine, phosphatidyl choline, phosphatidyl ethanolamine, and any mixture thereof. Optionally, the liposome may be prepared from a mixture of phospholipids including from about 5% to about 10% of a pegylated phospholipid. In one embodiment, the liposome may include from about 70% to about 95% (w/v) of a first phospholipid and from about 5% to about 10% (w/v) of a second, pegylated phospholipid. The chain length of the first phospholipid may be selected to be substantially the same as the chain length of the second, pegylated phospholipid.

In another aspect, a method is provided for administering a stable dispersion comprising a neutral camptothecin or analog thereof to an animal, including a human, in need thereof. The method is substantially as described above, with the further step of separating liposomes containing entrapped neutral camptothecins, prodrugs, or analogs thereof from any free drug before administering the liposome preparation. The liposome is then delivered to a patient in need thereof, whereby the liposome accumulates at a tumor site and the neutral camptothecin, prodrug, or analog thereof is released as an active, lactone form in situ at the tumor site.

In yet another aspect, a composition providing a therapeutically sufficient amount of a camptothecin, prodrug, or analog thereof, which may be a neutral camptothecin, for the treatment of a cancer in an animal, including a human, in need thereof is provided. The camptothecin, prodrug, or analog thereof is loaded into a liposome having an intraliposomal pH sufficient to maintain substantially an entirety of the intraliposomal neutral camptothecin, prodrug, or analog thereof in a carboxylate form. The methods for loading the camptothecin, prodrug, or analog into the liposome and the lipids and drugs suitable for preparing the composition, are substantially as described above. The composition may be formulated for delivery to a patient in need thereof, such as in an injectable formulation. Upon such delivery, the liposome comprising entrapped drug accumulates at and permeates into a tumor site. Over time, the camptothecin, prodrug or analog thereof is released as an active, lactone form in situ at the tumor site.

Other objects and applications of the present invention will become apparent to those skilled in this art from the following description wherein there is shown and described a preferred embodiment of this invention, simply by way of illustration of the modes currently best suited to carry out the invention. As it will be realized, the invention is capable of other different embodiments and its several details are capable of modification in various, obvious aspects all without departing from the invention. Accordingly, the drawings and descriptions will be regarded as illustrative in nature and not as restrictive.

BRIEF DESCRIPTION OF THE DRAWING

The accompanying drawing incorporated in and forming a part of the specification illustrates several aspects of the present invention and, together with the description, serves to explain the principles of the invention. In the drawing.

Figure 1:
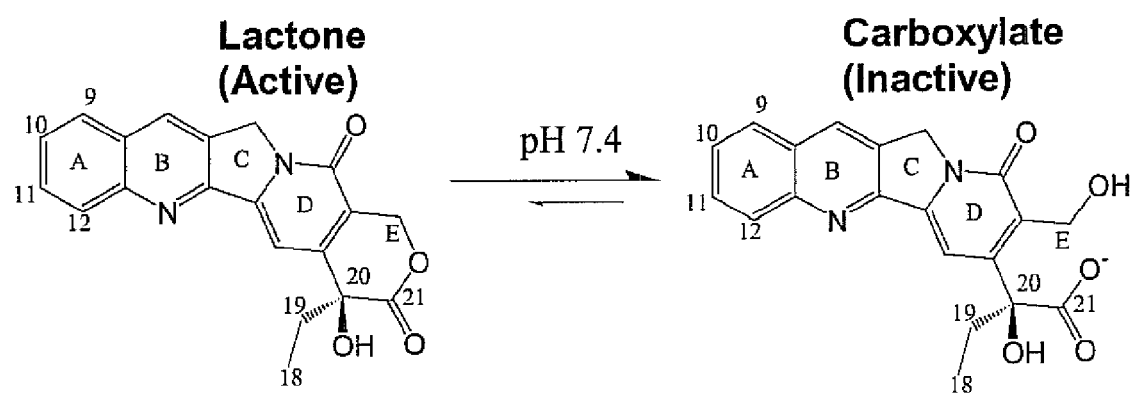
FIG. 1 depicts the reversible lactone ring-opening reaction in camptothecins.

Reference will now be made in detail to the presently preferred embodiments, examples of which are illustrated in the accompanying drawing.

DETAILED DESCRIPTION OF THE INVENTION

As summarized above, described herein are novel methods for providing liposomal formulations of camptothecins, camptothecin prodrugs, and analogs thereof, and compositions formulated thereby. It will be understood that the term camptothecin as used herein is intended to refer collectively to various camptothecins, camptothecin prodrugs, and camptothecin analogs as are well known in the art. The methods and compositions described herein may be accomplished by various means which are illustrated in the examples below. These examples are intended to be illustrative only, as numerous modifications and variations will be apparent to those skilled in the art.

It is known that at pH ranges which favor the lactone-form camptothecin, during liposomal encapsulation the drug preferentially partitions into liposomal membranes. This minimizes exposure to the aqueous environment, resulting in a decrease in ring opening of the active lactone. Accordingly, conventional liposomal formulations for camptothecins employ a low pH in liposomes to stabilize camptothecins in the active lactone form. However, this strategy requires use of an aqueous buffer to dissolve the drug prior to preparation of liposomes by conventional hydration-extrusion, sonication, or drug-lipid film techniques. Because of the low water-solubility of neutral camptothecins and the concomitant reductions in retention time for liposomal formulations of neutral camptothecins (see Table 1), such conventional strategies are more favorable to liposomal encapsulation of cationic camptothecins than neutral camptothecins.

TABLE 1

Percent retention vs. circulation time for investigational liposomal camptothecins

| Camptothecin | Status | % retention | |
|---|---|---|---|
| | | 4 hr | 24 hr |
| Lurtotecan[1] | Phase II | ~50 | <0.1 |
| Topotecan[2] | Preclinical | 23 | ~0 |
| Irinotecan[3] | Preclinical | 68* | 8* |

TABLE 1-continued

Percent retention vs. circulation time for investigational liposomal camptothecins

| Camptothecin | Status | % retention | |
|---|---|---|---|
| | | 4 hr | 24 hr |
| DB-67[4] | Preclinical | <1 | ND |
| SN-38[5] | Phase I/II | <1 | <0.1 |

[1]Emerson et al., 2000, Antitumor efficacy, pharmacokinetics, and biodistribution of NX-211: A low-clearance liposomal formulation of lurtotecan. Clin. Canc. Res. 6: 2903-2912; Colbern et al., 1998, Encapsulation of the topoisomerase I inhibitor GL147211C in pegylated (STEALTH) liposomes: pharmacokinetics and antitumor activity in HT29 colon tumor xenografts, Clin. Canc. Res. 4: 3077-3082.
[2]Tardi et al., 2000, Liposomal encapsulation of topotecan enhances anticancer efficacy in murine and human xenograft models. Cancer Res. 60: 3389-3393.
[3]Messerer et al., 2004, Liposomal irinotecan: formulation development and therapeutic assessment in murine xenograft models of colorectal cancer, Clin. Canc. Res. 10: 6638-6649.
[4]Zamboni et al., 2005, Plasma and tissue disposition of non-liposomal DB-67 and liposomal DB-67 in CB-17 SCID mice. Investigational New Drugs, published on-line February 2008 (DOI 10.1007/s10637-007-9109-9).
[5]Pal et al., 2005, Preclinical safety, pharmacokinetics and antitumor efficacy profile of liposome-entrapped SN-38 formulation, Anticancer Res. 25: 331-341.

Camptothecins, including neutral camptothecins, exist predominantly in the active lactone form in aqueous solution at pH less than 6.0, whereas the inactive carboxylate species dominates in aqueous solution at pH above 6.0. At physiological pH (7.4), approximately 70% of camptothecin is in the carboxylate form. Thus, in plasma, approximately 70% of the drug is in carboxylate (inactive) form and 30% in lactone (active) form. The half-life of lactone-form camptothecin in rat plasma is approximately 40 min. Encapsulating the lactone form of a representative neutral camptothecin, DB-67, in pegylated liposomes at low pH (4) prolongs the half-life of the drug. However, at this pH it was not possible to retain the drug in liposomes in aqueous buffers for long periods of time.

It has been found that preparing liposomes containing entrapped camptothecins, prodrugs, or analogs thereof, including neutral camptothecins, at a pH sufficient to keep substantially an entirety of the intraliposomal drug in the inactive carboxylate form significantly increased the half-life for retention in liposomes. This is because the release of the carboxylate form from the liposomes is negligible. Surprisingly, however, slow conversion of the entrapped, ring-opened carboxylate occurs, providing a low, steady-state concentration of lactone form drug which is then slowly released from the liposome. Thus, the present invention provides a slow and prolonged release of the active lactone form from the liposome. This release rate can be varied by changing the intraliposomal pH. That is, an increase in the intraliposomal pH slows the release of active lactone from the liposome, and vice-versa.

The compositions contemplated herein may be formulated for delivery to patients in need thereof using methods and formulations well within the skill in the art. For example, the compositions may be prepared for direct delivery, or as pharmaceutical formulations along with suitable carriers or excipients as are well known to the skilled artisan. For example, one or more additives may be included with the compositions, such as one or more stabilizers, buffers, salts, preservatives, fillers, and the like. Suitable buffers include without limitation phosphates, carbonates, citrates, and others. Suitable preservatives include without limitation EDTA, EGTA, BHA, BHT, and others.

The skilled artisan will also readily appreciate that pharmaceutical formulations comprising the present compositions will be highly dependent on the route of administration chosen. By way of non-limiting example, injectable formulations of the compositions may be provided as aqueous solutions, typically in physiologically compatible buffers such as Hank's solution, Ringer's solution, or physiological saline buffer. Pharmaceutical formulations intended for parenteral injection, e.g., by bolus injection or continuous infusion, may be provided in unit dosage form, e.g., in ampoules or in multi-dose containers, typically with an added preservative as set forth above.

EXAMPLES

Set forth in greater detail below are specific details related to selected modes for carrying out the methods and compositions of the present invention. The examples set forth herein are in no way intended to limit the scope of the invention. Those of skill in the art will realize that, given the teachings provided herein, many variations of the methods are possible that will fall within the scope of the present invention. Unless otherwise indicated, all citations of literature are specifically incorporated by reference herein in their entirety.

Example 1

Phospholipids and pegylated phospholipids were purchased as powders from Avanti Polar Lipids (Alabaster, Ala.). A representative neutral camptothecin, DB-67, was from Novartis Pharmaceutical Corp. (East Hanover, N.J.). Sprague-Dawley rat plasma was from Bioreclamation, Inc. (East Meadow, N.Y.). CENTRICON® (MWCO: 100000) centrifugal filter devices from Millipore (Billerica, Mass.) and SEPHADEX® G-25 M prepacked size exclusion columns (GE Healicare Bio-sciences Corp., Piscataway, N.J.) were used in liposome studies. All other reagents were from Fisher Scientific (Florence, Ky.).

Liposomes were prepared by conventional hydration-extrusion technique. However, the skilled artisan will appreciate that any suitable method for preparing liposomes having a desired particle size and lamellarity is contemplated. In one aspect, liposomes having a particle size range of from about 50 to about 300 nm are contemplated for use in the present invention. Methods for preparing liposomes falling within a predetermined size range are known in the art (see Drummond et al., 1999).

For the hydration-extrusion technique, films of the desired lipid mixtures were prepared in test tubes by dissolving weighed amounts of lipids in chloroform, evaporating the solvent under nitrogen, and drying overnight in vacuo. A stock solution of drug (DB-67) in a buffer providing the desired pH was added to hydrate the lipids, followed by shaking and extrusion through polycarbonate membranes at 60° C. to obtain unilamellar vesicles containing entrapped drug. Thus, intraliposomal pH of the final liposome-entrapped drug preparation prepared as described was substantially in accordance with the pH of the buffer/DB-67 solution in which phospholipid mixtures were hydrated.

Example 2

The liposomal permeability of DB-67 in aqueous solution was measured over a pH range of 4.5 to 9.5 using a dynamic dialysis method [V. Joguparthi and B. D. Anderson, Liposomal delivery of hydrophobic weak acids: Enhancement of drug retention using a high intraliposomal pH, J. Pharm. Sci. 97, 433-454 (2008)]. Liposome-encapsulated DB-67 solutions were prepared at varying pH values as described above. For liposome solutions at each pH evaluated, liposome-entrapped drug was separated from free drug by passing liposomes through a SEPHADEX® column followed by 5 mL of the same buffer added in 1 mL increments. The liposome-containing eluent was dialyzed at 37° C. in the same buffer. At intervals, 100 μl of liposome suspension was removed from the dialysis tube and added to 900 μl cold methanol/acetonitrile (2:1, v/v). These samples were dried under nitrogen and stored (−25° C.) prior to analysis.

With reference to Table 2, DB-67 was retained in liposomes (prepared by hydration-extrusion) in aqueous solution for increased periods of time when liposomes were prepared at high pH. In aqueous solution, the half-life for retention of DB-67 in liposomes increased from 3 hours at pH 4 to about 90 hours at pH 9.5. Without being restricted to any particular theory, this may be due to conversion of DB-67 lactone to the carboxylate form in the intraliposomal space.

TABLE 2

Half-life for liposome retention of DB-67 at various pH.

| pH | $t_{1/2}$ (hours) |
|---|---|
| 4 | 3 |
| 7.21 | 3.8 |
| 7.78 | 5.4 |
| 8.36 | 32.9 |
| 8.95 | 57.9 |
| 9.49 | 91.9 |

Figure 2:
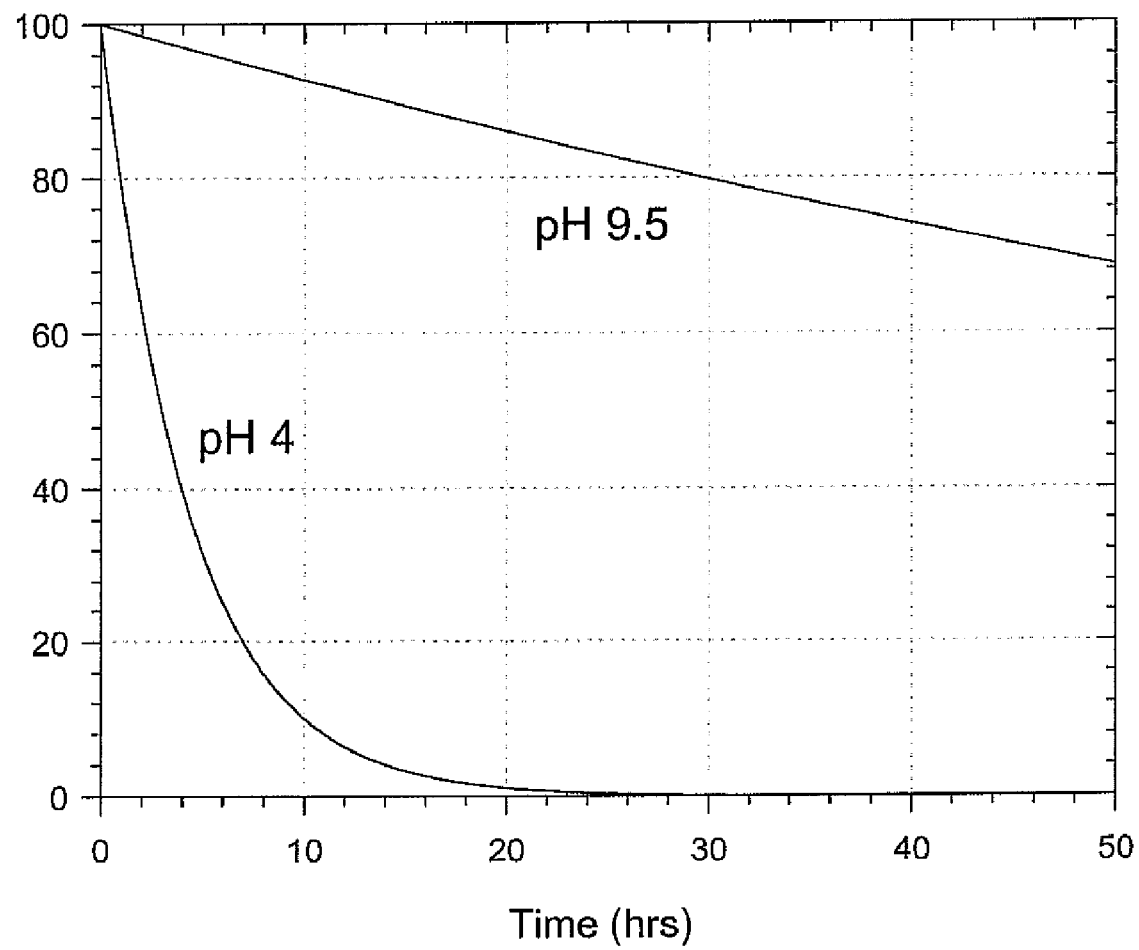
FIG. 2 shows liposomal release of DB-67 in aqueous solution at pH 4 vs. pH 9.5.

As shown in FIG. 2, when intraliposomal pH was maintained whereby the carboxylate species of DB-67 predominated, release of the drug from liposomes was negligible. For release to occur, pH conditions allowing formation of the active, lactone species were required.

Example 3

The efflux of DB-67 from liposomes in plasma was monitored. Aliquots of liposome suspension containing DB-67 (with unentrapped drug separated as described above) were added to plasma and incubated at 37° C. At intervals, an aliquot of plasma was withdrawn, added to cold methanol/acetonitrile (2:1 v/v), centrifuged (14000 rpm) and stored frozen (−25° C.) for HPLC analysis.

HPLC analyses used herein have been previously described in detail (Joguparthi et al., 2006). DB-67 carboxylate standards (10-100 nM) were prepared in 10 mM carbonate buffer (pH 10.4). DB-67 lactone standards (5-30 nM) were prepared in acidified methanol. All standards were diluted into the desired concentration range using cold methanol/acetonitrile (2:1 v/v). HPLC retention times were 1.6 and 5.2 min for DB-67 carboxylate and lactone, respectively.

Figure 3:
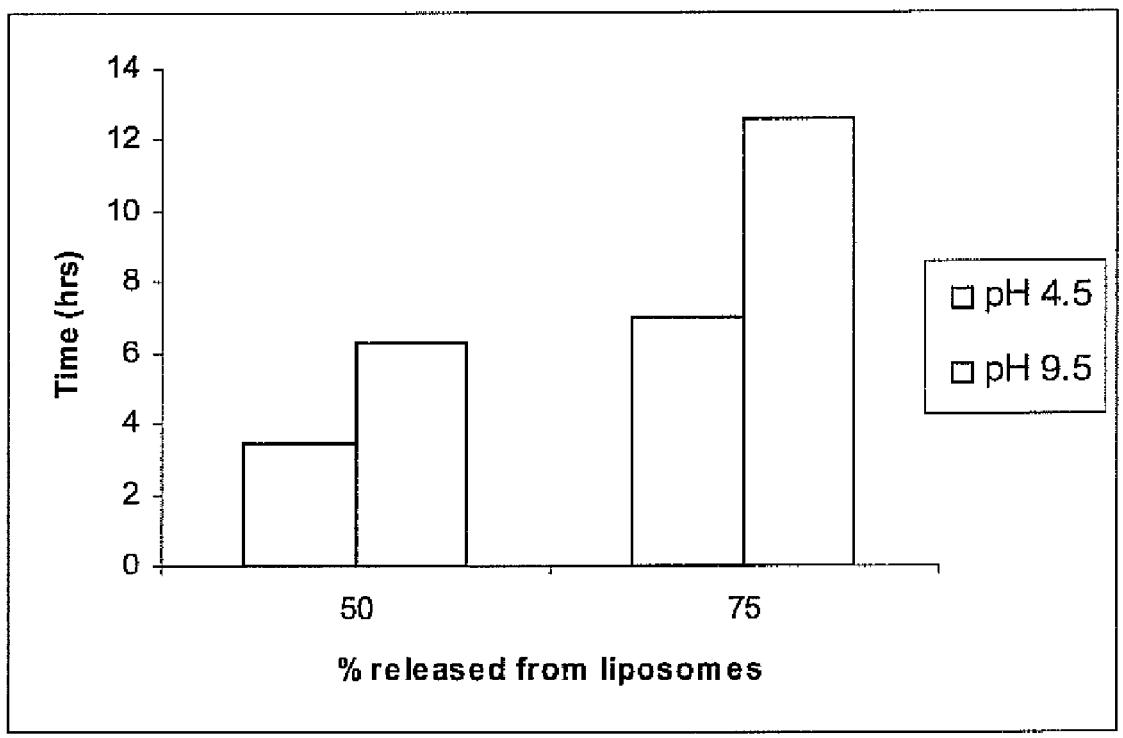
FIG. 3 shows liposomal release of DB-67 in plasma at pH 4.5 vs. pH 9.5.

FIG. 3 shows liposomal release of DB-67 in plasma at pH 4.5 and pH 9.5. In plasma, the half-life for retention in liposomes was 3.5 hours when intraliposomal pH was 4.5 and 6.3 hours when intraliposomal pH was 9.5. The half-life for retention at intraliposomal pH 9.5 was less in plasma than in aqueous solution due to a decrease in intraliposomal pH observed after adding liposomes to plasma. However, even in plasma, preparing liposomes at pH 9.5 and maintaining intraliposomal pH at levels which preserve the carboxylate form of the entrapped neutral camptothecin prolonged intraliposomal retention. Thus, the potential for exposure of healthy tissue to the drug was reduced. This improved intraliposomal retention enables the drug to remain in the liposomes while they are circulating in the bloodstream. After the liposomes collect in solid tumors due to their enhanced permeation across the tumor vasculature and their improved retention within the tumor tissue (Drummond et al., 1999), the entrapped drug will be slowly released as the active, lactone form of the drug directly at the tumor site, providing a significant enhancement in efficiency of delivery.

Example 4

A 10 mg/ml solution of DB-67 was prepared in pH 9.5 sodium carbonate buffer and filtered through a 0.2 μm syringe filter. The drug solution was used to hydrate phospholipids (DSPC+5 mol % m-PEG DSPE) with shaking at 60° C. to form a 30 mg/ml suspension of multilamellar vesicles. The suspension was extruded through a high pressure extruder to form unilamellar vesicles. The vesicles were then cooled at room temperature and stored below 5° C. until use. Prior to use, liposomes were separated from unentrapped DB-67 by passing through a gel filtration column which was pre-equilibrated with pH 7.4 phosphate buffered saline. 100 μl of liposomes collected from gel filtration were immediately added to 4 ml of plasma to study the release of liposome-entrapped DB-67 carboxylate from plasma as described above. Samples were taken at various time intervals and DB-67 was extracted from 100 μl of plasma using 300 μl of ice-cold methanol solution and acetonitrile (2:1 v/v) at −9° C. The concentration of DB-67 was determined by HPLC as described above.

Example 5

A 10 mg/ml solution of DB-67 was prepared in pH 9.5 sodium carbonate buffer and filtered through a 0.2 μm syringe filter. The drug solution was used to hydrate phospholipids (DSPC+5 mol % m-PEG DSPE) with shaking at 60° C. to form a 30 mg/ml suspension of multilamellar vesicles. The suspension was extruded through a high pressure extruder to form unilamellar vesicles. The vesicles were then cooled at room temperature and stored below 5° C. until use. Prior to use, liposomes were separated from unentrapped DB-67 by passing through a gel filtration column which was pre-equilibrated with pH 9.5 sodium carbonate buffer. The liposomes collected from gel filtration were immediately loaded into a dialysis tube and dialyzed (37 C) against 1000 ml of pH 9.5 sodium carbonate buffer. DB-67 analysis was by HPLC as described above.

Example 6

A 20 mg/ml solution of DB-67 is prepared in pH 10.5 sodium carbonate buffer and filtered through a 0.2 μm syringe filter. The drag solution is used to hydrate phospholipids (DSPC+5 mol % m-PEG DSPE) with shaking at 60° C. to form a 30 mg/ml suspension of multilamellar vesicles. The suspension is extruded through a high pressure extruder to form unilamellar vesicles. The vesicles are then cooled at room temperature and stored below 5° C. until use. Prior to use, liposomes are warmed to room temperature and separated from unentrapped DB-67 by gel filtration as described.

Example 7

10 mg of DB-67 is added to 60 mg of a phospholipid mixture in 2 ml of a 2:1 mixture of chloroform:ethanol. The solution is evaporated under nitrogen to form a drug-lipid film. The film is hydrated with pH 10.5 carbonate buffer with shaking to form multilamellar vesicles. The suspension is extruded to form unilamellar vesicles. The vesicles are cooled to room temperature and unentrapped drug is separated from entrapped drug as described. The liposomes are then stored below 5° C. until use.

Example 8

Drug is loaded in vesicles as described in Examples 6 and 7, except the drug and phospholipids are dissolved in pure chloroform, pure acetone, pure methanol, or a suitable combination of those solvents. Subsequently, solvent is evaporated to form a drug-lipid film.

Example 9

Unilamellar vesicles are prepared as described in Examples 4-8 using pH 9.5 borate buffer.

Example 10

Unilamellar vesicles are prepared as described in Examples 4-8 using pH 9.5 Tris-HCl buffer.

Example 11

Unilamellar vesicles are prepared as described in Examples 4-8 using pH 9.3 ammonium hydroxide.

Example 12

Unilamellar vesicles are prepared as described in Examples 4-8 using pH 9 glycine.

Example 13

Unilamellar vesicles are prepared as described in Examples 4-12, with the exception that the vesicles are formed by sonication rather than extrusion.

Example 14

Unilamellar vesicles are prepared as described in Examples 4-13, except the drug used is SN-38.

Example 15

Unilamellar vesicles are prepared as described in Examples 4-13, except the drug used is karenitecan.

Example 16

Unilamellar vesicles are prepared as described in Examples 4-13, except the drug used is gimatecan.

Example 17

Unilamellar vesicles are prepared as described in Examples 4-13, except the drug used is 9-nitro camptothecin.

Example 18

Unilamellar vesicles are prepared as described in Examples 4-17, with the exception that during separation of entrapped from unentrapped drug, the extraliposomal buffer is exchanged for pH 7.4 phosphate with the proviso that intraliposomal pH is maintained the same as that used in liposome preparation.

Example 19

Unilamellar vesicles are prepared as described in Examples 4-17, with the exception that during separation of entrapped from unentrapped drug, the extraliposomal buffer is exchanged for a desired concentration of NaCl solution with the proviso that intraliposomal pH is maintained the same as that used in liposome preparation.

Example 20

Unilamellar vesicles are prepared as described in Examples 4-17, with the exception that during separation of entrapped from unentrapped drug, the extraliposomal buffer is exchanged for a desired concentration of sucrose solution, with the proviso that intraliposomal pH is maintained the same as that used in liposome preparation.

Example 21

Unilamellar vesicles are prepared as described in Examples 4-20, using a lipid mixture comprising 80% DSPC, 15% cholesterol, and 5% m-PEG DSPE.

Example 22

Unilamellar vesicles are prepared as described in Examples 4-20, using a lipid mixture comprising 80% HSPC, 15% cholesterol, and 5% pegylated PE.

Example 23

Unilamellar vesicles are prepared as described in Examples 4-20, using a lipid mixture comprising 55% DSPC, 40% cholesterol, and 5% m-PEG DSPE.

The skilled artisan will readily appreciate that the present disclosure sets forth an efficient and efficacious method for preparing a liposomal formulation of a camptothecin, in one aspect being a neutral camptothecin, camptothecin prodrug, or analog thereof. Advantageously, the compositions formulated by the present method provide a stable liposomal camptothecin in therapeutically effective amounts, wherein the drug is retained in the liposome under physiological conditions for increased periods of time. This allows accumulation of the liposomal camptothecin formulations at a tumor site, with limited side effects on healthy cells and tissue, and further allows in situ delivery of the active lactone form of the drug to directly to tumor tissue in adequate concentrations for effective tumor cell killing and/or growth inhibition.

By increasing intraliposomal pH and maintaining that pH prior to administration and during in vivo delivery to a tumor site, it has been surprisingly found that liposomal retention of a camptothecin may be prolonged, reducing the potential for exposure of healthy tissue to the drug when administered in vivo. This improvement in retention allows the drug to accumulate at tumor tissue, i.e., an in vivo enhanced permeation and retention effect (Drummond et al., 1999). As the liposomes accumulate within the tumor tissue, over time the drug is released as the lactone form in situ, thus achieving release of drug in the active form directly at the tumor site, rather than drug residing in the bloodstream at physiological conditions favoring conversion to the inactive carboxylate form. Accordingly, the problems of enhanced liposomal retention and delivery of the active lactone form camptothecin to a tumor site are simultaneously solved.

The foregoing description of preferred embodiments has been presented for purposes of illustration and description. It is not intended to be exhaustive or limiting to the precise forms disclosed. Obvious modifications or variations are possible in light of the above teachings. The embodiments were chosen and described to provide the best illustration of the principles described herein and their practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method for preparing a stable dispersion of a camptothecin or analog thereof for delivery to a patient in need thereof, comprising:
preparing a solution of a camptothecin, camptothecin prodrug, or analog thereof, said solution having a pH which places substantially an entirety of that camptothecin or analog thereof in a carboxylate form;
loading the solution of camptothecin, camptothecin prodrug, or analog thereof into a liposome comprised of at least one lipid, said liposome having an intraliposomal pH which preserves substantially an entirety of said camptothecin, camptothecin prodrug, or analog thereof in the carboxylate form, said at least one lipid being selected to provide to said liposome a net neutral or anionic charge; and
delivering said liposome loaded with said carboxylate form camptothecin, camptothecin prodrug, or analog thereof to a patient in need thereof, whereby said liposome accumulates at a tumor site and said camptothecin, camptothecin prodrug, or analog thereof is released as an active, lactone form in situ at said tumor site.

2. The method of claim 1, wherein the solution of camptothecin, camptothecin prodrug, or analog thereof is formulated to have a pH of from about 8.0 to about 11.0.

3. The method of claim 1, wherein the lipid is selected from at least one of a phospholipid and a sterol.

4. The method of claim 3, wherein the phospholipid is selected from the group consisting of an egg phospholipid, a soy phospholipid, distearoylphosphatidyl choline, dipalmitoylphosphatidyl choline, diarachidonoyl phosphatidyl choline, hydrogenated soy phosphatidyl choline, dimyristoylphosphatidyl glycerol, dioleylphosphatidylglycerol, dimyristoylphosphatidylcholine, phosphatidyl choline, phosphatidyl ethanolamine, and mixtures thereof.

5. The method of claim 1, wherein said liposome comprises a mixture of phospholipids including from about 5% to about 10% of a pegylated phospholipid.

6. The method of claim 4, wherein said liposome comprises from about 70% to about 95% (w/v) of a first phospholipid and from about 5% to about 10% (w/v) of a second, pegylated phospholipid.

7. The method of claim 6, wherein a chain length of the first phospholipid is substantially the same as a chain length of the second, pegylated phospholipid.

8. The method of claim 1, wherein the camptothecin, camptothecin prodrug or analog thereof is selected from the group of neutral camptothecins, camptothecin prodrugs, and analogs consisting of camptothecin, DB-67, SN-38, gimatecan, irinotecan, karenitecin, 9-nitro camptothecin, and mixtures thereof.

9. A method for administering a stable solution of a neutral camptothecin, camptothecin prodrug, or analog thereof to a patient in need thereof, comprising:
preparing a solution of a neutral camptothecin, camptothecin prodrug, or analog thereof, said solution having a pH which places substantially an entirety of that neutral camptothecin, camptothecin prodrug, or analog thereof in substantially a carboxylate form;
loading the solution of neutral camptothecin, camptothecin prodrug, or analog thereof into a liposome comprised of at least one lipid, said liposome having an intraliposomal pH which preserves substantially an entirety of said neutral camptothecin, camptothecin prodrug, or analog thereof in the carboxylate form, said at least one lipid being selected to provide to said liposome a net neutral or anionic charge;
separating the liposome from any free neutral camptothecin, camptothecin prodrug, or analog thereof; and
administering the liposome loaded with said carboxylate form neutral camptothecin, camptothecin prodrug, or analog thereof to a patient in need thereof whereby the liposome accumulates at a tumor site and said neutral camptothecin, camptothecin prodrug, or analog thereof is released as an active, lactone form in situ at said tumor site.

10. The method of claim 9, wherein the solution of neutral camptothecin, camptothecin prodrug, or analog thereof is formulated to have a pH of from about 8.0 to about 11.

11. The method of claim 9, wherein the lipid is selected from at least one of a phospholipid and a sterol.

12. The method of claim 11, wherein the phospholipid is selected from the group consisting of an egg phospholipid, a soy phospholipid, distearoylphosphatidyl choline, dipalmitoylphosphatidyl choline, diarachidonoyl phosphatidyl choline, hydrogenated soy phosphatidyl choline, dimyristoylphosphatidyl glycerol, dioleylphosphatidylglycerol, dimyristoylphosphatidylcholine, phosphatidyl choline, phosphatidyl ethanolamine, and mixtures thereof.

13. The method of claim 9, wherein said liposome comprises a mixture of phospholipids including from about 5% to about 10% of a pegylated phospholipid.

14. The method of claim 12, wherein said liposome comprises from about 70% to about 95% (w/v) of a first phospholipid and from about 5% to about 10% (w/v) of a second, pegylated phospholipid.

15. The method of claim 14, wherein a chain length of the first phospholipid is substantially the same as a chain length of the second, pegylated phospholipid.

16. The method of claim 9, wherein the neutral camptothecin, camptothecin prodrug, or analog thereof is selected from the group consisting of camptothecin, DB-67, SN-38, gimatecan, karenitecin, irinotecan, 9-nitro camptothecin, and mixtures thereof.

17. A composition comprising a therapeutically sufficient amount of a camptothecin, camptothecin prodrug, or analog thereof for the treatment of a cancer in an animal in need thereof, said camptothecin, camptothecin prodrug, or analog thereof being loaded into a liposome having an intraliposomal pH sufficient to maintain substantially an entirety of the intraliposomal camptothecin, camptothecin prodrug, or analog thereof in a carboxylate form for delivery to said animal, wherein said liposome is comprised of lipids whereby said liposome has a net neutral or anionic charge.

18. The composition of claim 17, wherein the intraliposomal pH is from about 8.0 to about 11.0.

19. The composition of claim 7, wherein the liposome comprises at least one of a phospholipid and a sterol.

20. The composition of claim 19, wherein the phospholipid is selected from the group consisting of an egg phospholipid, a soy phospholipid, distearoylphosphatidyl choline, dipalmitoylphosphatidyi choline, diarachidonoyl phosphatidyl choline, hydrogenated soy phosphatidyl choline, dimyristoylphosphatidyi glycerol, dioleylphosphatidylglycerol, dimyristoylphosphatidylcholine, phosphatidyl choline, phosphatidyl ethanolamine, and mixtures thereof.

21. The composition of claim 19, wherein the liposome comprises a mixture of phospholipids including from about 5% to about 10% of a pegylated phospholipid.

22. The composition of claim 21, Wherein the liposome comprises from about 70% to about 95% (w/v) of a first phospholipid and from about 5% to about 10% (w/v) of a second, pegylated phospholipid.

23. The composition of claim 22, wherein a chain length of the first phospholipid is substantially the same as a chain length of the second, pegylated phospholipid.

24. The composition of claim 17, wherein the camptothecin, camptothecin prodrug, or analog thereof is selected from the group of neutral camptothecins, camptothecin prodrugs, and analogs consisting of camptothecin, DB-67, SN-38, gimatecan, karenitecin, irinotecan, 9-nitro camptothecin, and mixtures thereof.

* * * * *